(12) United States Patent
Amélia

(10) Patent No.: US 9,302,123 B2
(45) Date of Patent: Apr. 5, 2016

(54) GANTRY STRUCTURE FOR A HADRON THERAPY APPARATUS

(71) Applicant: Ion Beam Applications S.A., Louvain-la-Neuve (BE)

(72) Inventor: Jean-Claude Amélia, Erquelinnes (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 0 days.

(21) Appl. No.: 14/366,541

(22) PCT Filed: Dec. 21, 2012

(86) PCT No.: PCT/EP2012/076682
§ 371 (c)(1),
(2) Date: Jun. 18, 2014

(87) PCT Pub. No.: WO2013/093020
PCT Pub. Date: Jun. 27, 2013

(65) Prior Publication Data
US 2014/0357930 A1 Dec. 4, 2014

(30) Foreign Application Priority Data
Dec. 21, 2011 (EP) .................................. 11195065
May 9, 2012 (EP) .................................. 12167394

(51) Int. Cl.
*A61N 5/10* (2006.01)

(52) U.S. Cl.
CPC ....... *A61N 5/1081* (2013.01); *A61N 2005/1087* (2013.01)

(58) Field of Classification Search
USPC ...................................................... 250/492.1
See application file for complete search history.

(56) References Cited

U.S. PATENT DOCUMENTS

| 4,507,616 A | 3/1985 | Blosser et al. |
| 2004/0184579 A1* | 9/2004 | Mihara ............... A61N 5/10 378/65 |

(Continued)

FOREIGN PATENT DOCUMENTS

| EP | 0986070 A1 | 3/2000 |
| EP | 2058027 A1 | 5/2009 |
| EP | 2308561 A1 | 4/2011 |

OTHER PUBLICATIONS

International Search Report and Written Opinion of the International Searching Authority, International Application No. PCT/EP2012/076682, Date of completion of the search Mar. 1, 2013, 10 pages.

(Continued)

*Primary Examiner* — Phillip A Johnston
(74) *Attorney, Agent, or Firm* — Fitch, Even, Tabin & Flannery LLP

(57) ABSTRACT

A gantry structure (16) designed for pivoting about an axis of rotation (18) and for delivering a hadron beam on a target comprises a beam delivery line (24) receiving the hadron beam in a direction essentially parallel to the axis of rotation (18), deviating it away from said axis of rotation (18) and delivering it so that the axis of the beam intersects the axis of rotation (18). The beam delivery line (24) is a self-supporting structure supported by a pivotable support arm (32) in proximity of the center of gravity of the beam delivery line (24). A counterweight (42) is supported by a support arm extension (40) on the other side of the axis of rotation (18) for compensating the moment of force due to the weight of the beam delivery line (24) and the support arm (32).

19 Claims, 4 Drawing Sheets

(56) References Cited

U.S. PATENT DOCUMENTS

2007/0029510 A1* 2/2007 Hermann ................ A61N 5/10
250/493.1
2010/0163755 A1* 7/2010 Takeda ................... A61N 5/10
250/492.3

OTHER PUBLICATIONS

Weinrich, "Gantry Design for Proton and Carbon Hadrontherapy Facilities." Proceedings of EPAC 2006, Edinburgh, Scotland, 07 Accelerator Technology, pp. 964-968.

* cited by examiner

GANTRY STRUCTURE FOR A HADRON THERAPY APPARATUS

CROSS REFERENCE TO RELATED APPLICATIONS

This is a U.S. national phase application of International Application No. PCT/EP2012/076682, filed Dec. 21, 2012, designating the United States and claiming priority to European Patent Application No. 11195065.5, filed Dec. 21, 2011, and European Patent Application No. 12167394.1, filed May 9, 2012, which are incorporated by reference in their entireties.

TECHNICAL FIELD

The present invention relates to a gantry structure for a hadron therapy apparatus and to a hadron therapy apparatus with a compact gantry structure.

DESCRIPTION OF RELATED ART

Radiotherapy using charged particles (e.g. protons, carbon ions, . . . ) has proven to be a precise and conformal radiation therapy technique, which allows to deliver a high dose to a target volume, while minimizing the dose to surrounding healthy tissues. In general, a particle therapy facility comprises an accelerator producing energetic charged particles, a beam transport system for guiding the particle beam to one or more treatment rooms and, for each treatment room, a particle beam delivery system. There are basically two types of beam delivery systems. Fixed beam delivery systems deliver the beam to the target volume from a fixed irradiation direction. Rotating beam delivery systems are capable of delivering the beam to the target volume from multiple irradiation directions. Such a rotating beam delivery system is also named gantry. The target volume is generally positioned at a fixed position defined by the crossing of the axis of rotation of the gantry and the central axis of the treatment beam. This crossing point is called isocenter, and gantries of this type capable of delivering beams from various directions onto the isocenter are called isocentric gantries.

The gantry beam delivery system comprises devices for shaping the beam to match the target volume. There are two major techniques used in particle beam therapy to shape the beam: (i) the more common passive scattering techniques; and (ii) the more advanced dynamic radiation techniques. An example of a dynamic radiation technique is the so-called pencil beam scanning (PBS) technique. In PBS a narrow pencil beam is magnetically scanned across a plane orthogonal to the central beam axis. Lateral conformity in the target volume is obtained by adequate control of the scanning magnets. Depth conformity in the target volume is obtained by adequate control of the beam energy. In this way, a particle radiation dose can be precisely delivered to the entire 3D target volume.

Applicant's European patent EP 2308561 (B), the disclosure of which is incorporated herein by reference, describes the state of the art in the field of gantries for hadron therapy.

A recent overview of gantries for proton and carbon therapy is given by U. Weinrich in "Gantry design for proton and carbon hadrontherapy facilities", Proceedings of EPAC 2006 (European Particle Accelerator Conference), Edingburgh, Scotland. As shown, all proton isocentric gantries have longitudinal dimensions between 9 and 12 m and have a maximum radial displacement of the beam from the gantry axis of rotation that varies between 3.2 m and 5 m.

A common drawback of all known isocentric gantries is that they are cumbersome, require a lot of space and represent for hospitals a huge investment.

Compared to previous gantries, the gantry disclosed in EP 2308561 (B) presents many advantages. For example: the diameter and length of the gantry are strongly reduced; the heavier gantry elements are positioned closer to the axis of rotation; and the center of gravity of the dipole magnets at the end of the beam line are closer to the axis of rotation, which results in less constraints for the mechanical support structure and makes the latter less expensive.

The mechanical support structure of the gantry disclosed in EP 2308561 (B) has however some drawbacks too. As is best seen in FIG. 5 of EP 2308561 (B), the mechanical support structure of the gantry is a cumbersome frame supporting the beam delivery line on one side of the axis of rotation and a heavy counterweight on the other side of the axis of rotation. This cumbersome frame has to be rigid enough to support at least the weight of two heavy bending magnets and the heavy counterweight. This frame is itself supported by two large diameter roller support bearings. A first of these roller support bearings is located near the entrance point of the beam into the beam delivery line, in a tight space between a shielding wall and a drum structure comprising a first bending magnet and a cable spool. A second roller support bearing is spaced several meters from the first roller support bearing and located below the second bending magnet. It follows that both roller support bearings are very unequally loaded.

US 2007/029510 discloses a gantry system in which the beam guidance gantry 12 (called herein the beam delivery line) is supported by a support structure comprising a so-called outer gantry ring 31, which is supported in a huge diameter bearing ring 17 and supports the beam guidance gantry at the level of its center of gravity, and a massive support arm 16, which extends from the outer gantry ring 31 to the beam inlet end of the beam guidance gantry 12, where it is supported in a bearing 19 and supports the beam inlet end of the beam guidance gantry 12. Such a gantry system is at least as cumbersome as the gantry system disclosed in EP 2308561 (B).

EP 2058027 A1 discloses a gantry system in which the beam delivery line is supported by a large diameter gantry cylinder, which is supported via a front ring 3, a rear ring 4 and an intermediate ring 5 on rotating body support devices 16a, 16b and 16c equipped with rollers 12. Such a gantry system is very cumbersome too.

A similar remark applies to EP 0986070 A1, which shows in FIG. 6 a gantry system in which the beam delivery line is supported by a support structure supported itself on large diameter cylinder.

Finally, U.S. Pat. No. 4,507,616 discloses a radiation therapy apparatus in which a superconducting cyclotron is directly supported by a rotatable balance bar 13. Such a device does of course not need a support structure for a beam delivery line, because it does not include a beam delivery line. However, it is obviously even a more cumbersome equipment than the prior art device discussed above.

There is consequently a first challenge for providing a more compact gantry structure for a hadron therapy apparatus than these prior art devices.

There is another challenge for providing such a compact gantry structure in which the support structure is subjected to more equal loads.

There is a still another challenge for providing such a compact gantry structure with a support structure that can be more easily integrated into a treatment room.

There is a further challenge for providing a such a gantry structure that can be easily transported, easily introduced into the treatment room and easily assembled in situ.

There is a further challenge for providing a gantry structure with a support structure warranting an easy access to the sub-equipments it supports.

SUMMARY OF THE INVENTION

A gantry structure according to the invention is designed for rotating or pivoting about an axis of rotation and for delivering a hadron beam, generated by a hadron accelerator, onto a target volume, normally located at an isocenter on the axis of rotation. This gantry structure comprises a beam delivery line receiving the hadron beam at a first end in a direction essentially parallel to the axis of rotation, deviating it away from the axis of rotation and delivering it at a second end so that its axis intersects the axis of rotation, normally at the isocenter. The gantry structure further comprises a counterweight on the other side of the axis of rotation for compensating the moment of force due to the weight of the beam delivery line and the support arm. In accordance with one aspect of the invention, the beam delivery line is a self-supporting structure supported by a pivotable support arm in proximity of its center of gravity, and said support arm is itself supported in a support structure, preferably near the axis of rotation, so as to be pivotable about the latter. The counterweight is supported by a support arm extension. It will be appreciated that a self-supporting beam delivery line directly supported near its center of gravity by a pivotable support arm, which is itself pivotably supported in a support structure, preferably in proximity of the axis of rotation and close to the center of the gantry structure, and in which the counterweight is supported by an extension of the support arm, is a far less cumbersome solution than the prior art gantries, in which a bulky rotating frame, cage or cylinder is used to support the beam delivery line at several axially spaced points. Furthermore, due to the absence of bulky rotating frame, cage or cylinder for the beam delivery line and the absence of large, the gantry structure can be more efficiently integrated into a treatment room, which helps reducing the overall costs of a hadron therapy facility. The gantry structure can be easily designed as a set of preassembled modules that can be easily shipped, easily introduced into the future treatment room and faster assembled therein.

The beam delivery line is advantageously supported by the pivotable support arm symmetrically with regard to a plane perpendicular to the axis of rotation and containing the center of gravity of the beam delivery line. This symmetry results in better optimization possibilities of the mechanical design of the support structure. It results e.g. in more equilibrated and simpler load distribution in the support structure, which makes mechanical deflections easier avoidable and residual mechanical deflections more predictable, thereby reducing positioning errors due to variable mechanical deflections and/or making them at least more predictable.

The support arm extension supporting the counterweight is preferably detachably connected to the support arm.

A preferred support structure comprises two support elements, which are preferably symmetric with regard to a plane perpendicular to the axis of rotation, said plane containing the center of gravity of the beam delivery line. The two support elements are preferably located close to said plane with the necessary gap between them for arranging therein the pivotable support arm. The pivotable support arm is advantageously arranged between the two supports elements and supported by the latter on two sides, in proximity of the axis of rotation. In this support structure, both support elements are subjected to equal or at least nearly equal loads. The horizontal distance between the two support elements is normally less than 50%, and preferably less than 35%, of the horizontal distance between the entrance point of the beam into the beam delivery line and the isocenter. Preferably, the gap between the two support elements in which the support arm is pivotable is dimensioned so that the distance between the pivotable support arm and each of the said support elements is less than 2 m 50, preferably less than 2 m.

Each of these support elements advantageously supports a support bearing, of a relatively small diameter, in which a bearing pivot of the pivotable support arm is received. Both support bearings are preferably substantially symmetric with regard to a plane perpendicular to the axis of rotation and containing the center of gravity of the beam delivery line. In such a preferred support structure, both support bearings are easily accessible because they are both located substantially near the center of the gantry structure, i.e. where the clearance is the highest. Both support bearings are moreover subjected to equal or at least nearly equal loads.

Each of the aforementioned support elements advantageously includes: a lower part for supporting it on a supporting surface; an upper part with a lateral fixing arm for fixing it to a lateral structure; and a cantilever support arm arranged between the lower part and the upper part for supporting the pivotable support arm at the opposite side of the lateral fixing arm at a certain horizontal distance (e) from the lower part. In this support element, the cantilever support arm can support the pivotable support arm so as to allow the beam delivery line to rotate about the axis of rotation by an angle greater than 180°, so that the beam delivery line is capable of passing in lower position (i.e. under the isocenter) through a vertical plane containing the axis of rotation. The lateral fixing arm allows compensating in a very effective way the important tilting moment due to the cantilevered support of the support bearing. Such a support structure allows an easy integration of the gantry structure into a treatment room, which helps of course to reduce the overall costs of a hadron therapy facility.

The beam delivery line is preferably capable of rotating about the axis of rotation between an angular position of $-\alpha°$ and an angular position of $+\beta°$, wherein theses angles are measured with respect to a vertical plane containing the axis of rotation, an angle of 0° corresponding to the position when the beam delivery line is in its upmost position. Preferred ranges for $\alpha°$ and $\beta°$ are e.g.: $15° \leq \alpha \leq 45°$ and $180° \leq \beta \leq 200°$. In a preferred embodiment, the beam delivery line is e.g. capable of rotating about the axis of rotation between an angular position of about $-35°$ and an angular position of about $+190°$.

The beam delivery line usually includes a sufficient number of bending magnets for defining a path for the hadron beam and a sufficient number of quadrupole magnets for focusing and/or defocusing the particle beam in the beam delivery line.

To achieve a hadron therapy apparatus with a gantry that can be easily transported, easily introduced into the treatment room and easily assembled in situ, the gantry preferably consists of a few gantry modules preassembled at the facility of the manufacturer and ready for being easily assembled in situ, i.e. in the future treatment room. A preferred gantry comprises a first preassembled gantry module consisting of the beam delivery line and the pivotable support arm, both already assembled. A second, complementary gantry module consists of the support arm extension and, optionally, the counterweight, wherein the support arm extension and the support arm are both equipped for being easily connectable in situ.

A preferred beam delivery line consists e.g. of an assembly of three successive units: a first beam line unit containing in particular a first bending magnet and at least two quadrupole magnets; a second beam line unit containing in particular at least two quadrupole magnets and a second bending magnet; and a third beam line unit containing in particular a third bending magnet. Preferably, the first beam line unit comprises a portion coaxial with the axis of rotation for receiving the hadron beam.

The pivotable support arm has a first side facing the inlet of the hadron beam into the beam delivery line, a second side facing the outlet of the hadron beam of the beam delivery line and a top side. The first beam line unit is preferably supported on the first side of the support arm. The second beam line unit is preferably supported on the top side of the pivotable support arm, so as to form a cantilever on the second side of the pivotable support arm. This cantilever may e.g. represent more than 50% of the length of the second beam line unit. The third beam line unit is most often a curved unit, which is supported in a cantilever manner by the second beam line unit.

The third beam line unit usually further includes a nozzle for delivering the hadron beam onto the isocenter. The second beam line unit may further include a scanning magnet.

Near the beam inlet end, the beam delivery line is advantageously supported in an auxiliary inlet support, which is preferably adjustable and warrants that the beam inlet end of the pivotable beam delivery line is centered with regard to the terminal section of the fixed beam transport line to which it is connected. This auxiliary inlet support is advantageously a roller support located beneath the beam inlet end, where it cooperates with a cylindrical bearing surface arranged on the beam inlet end for centering the latter on the axis of rotation. It will be appreciated that the load to be supported by the auxiliary inlet support is only a very small fraction of the load supported by the pivotable support arm, so that this auxiliary inlet support is not very bulky.

BRIEF DESCRIPTION OF DRAWINGS

An embodiment of the present invention will now be described by way of example with reference to the accompanying drawings, in which.

DESCRIPTION OF EMBODIMENTS

Figure 1:
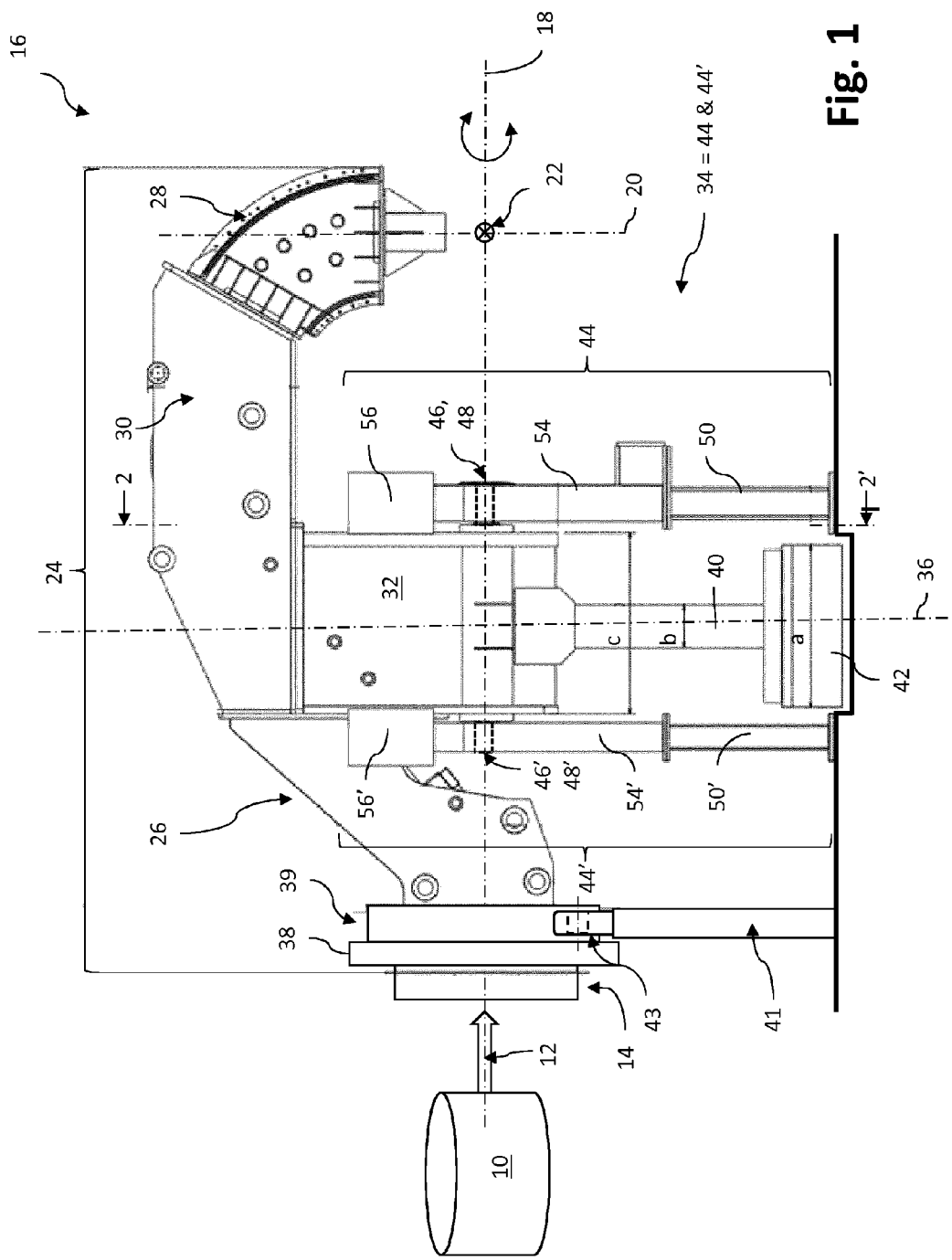
FIG. 1: is a schematic elevation view of a hadron beam apparatus with a gantry structure in accordance with the present invention.

FIG. 1 shows a hadron therapy apparatus with a gantry structure in accordance with the present invention. Cylinder 10 schematically represent a hadron accelerator (not drawn to scale), which generates a beam of accelerated hadrons (schematically represented by arrow 12) guided through a beam transport line (represented by its terminal section 14).

Arrow 16 globally identifies a gantry structure of the hadron therapy apparatus. Whereas the beam transport line 14 is immobile, the gantry structure 16 connected to the beam transport line 14 is capable of pivoting about a horizontal axis of rotation 18. This pivotable gantry structure 16 is used to deliver the hadron beam from different angular positions onto a target volume, wherein the central axis of the beam is always contained in a plane 20 that is perpendicular to the axis of rotation 18 and intersects the axis of rotation 18 at a point 22, called isocenter 22. The target volume (e.g. a tumor to be irradiated) is centered at the isocenter 22 on the axis of rotation 18 of the gantry structure 16. The patient lies hereby on a patient positioning system (not shown in the drawings) that allows centering the target volume at the isocenter 22 of the gantry structure.

Reference number 24 globally identifies a beam delivery line of the gantry structure 16. Through the end section 14 of the fixed beam transport line, the hadron beam 12 enters into an inlet section 26 of the beam delivery line 24 in a direction essentially parallel to the axis of rotation 18. In this inlet section 26, the beam is deviated away from the axis of rotation 18, so as to free sufficient place around the axis of rotation 18 for the patient positioning system. The deviation angle ($\alpha_1$) of the beam in this inlet section 26 is e.g. about 30° to 40°, in a preferred embodiment e.g. 36°. At the other end of the beam delivery line 24, an outlet section 28 deviates the beam again towards the axis of rotation 18, so that the axis of the beam is finally located in the plane 20 passing, normally, through the isocenter 22, i.e. the beam is essentially perpendicular to the axis of rotation 18 and passes normally through the isocenter 22. The deviation angle ($\alpha_2$) of the beam in this outlet section 28 is advantageously smaller than 90°, e.g. typically about 60°. The aforementioned inlet section 26 and outlet section 28 of the beam delivery line 24 are interconnected by a middle section 30. At the entrance of the middle section 30, the beam has a direction pointing away from the axis of rotation 18. In the middle section 30, the beam is gradually inflected to have at its outlet a direction pointing towards the axis of rotation 18. The deviation angle of the beam in this middle section 30 corresponds to $\alpha_1+90°-\alpha_2$, for example to 66°, if $\alpha_1=36°$ and $\alpha_2=60°$.

The inlet section 26 and the outlet section 28 of the beam delivery line 24 are both supported by a support arm 32, which is supported itself in a support structure (globally identified with reference number 34), so as to be pivotable about the axis of rotation 18. Reference number 36 identifies a plane of symmetry of the support arm 32 that is perpendicular to the axis of rotation 18. This plane of symmetry 36 advantageously contains the center of gravity of the beam delivery line 24. It follows that the pivotable support arm 32 is basically not subjected to an important bending moment in a plane containing the axis of rotation 18 and the center of gravity of the beam delivery line 24.

It will be noted that the inlet section 26 of the beam delivery line 24 is connected to the end section 14 of the fixed beam transport line by means of a rotating joint 38. A radial play between in this rotating joint 38 warrants that the end section 14 of the fixed beam transport line does not exert any major force onto the beam delivery line 24 supported by the pivotable support arm 32.

At the beam inlet end, near the rotating joint 38, the inlet section 26 is moreover supported in an auxiliary inlet support 41, 43. The latter warrants that the beam inlet end of the pivotable beam delivery line 24 is exactly centered with regard to the end section 14 of the fixed beam transport line to which it is connected. This auxiliary inlet support is e.g. a roller support 43 located beneath the beam inlet end of the beam delivery line 24, on which the beam inlet section 26 of the beam delivery line rests by means of a cylindrical bearing surface 39. The roller support 43 includes e.g. two adjustable rollers arranged symmetrically with regard to a vertical plane containing the axis of rotation 18. By adjusting the position of the rollers, one may correct a misalignment between the beam inlet end of the pivotable beam delivery line 24 and the end section 14 of the fixed beam transport line to which it is connected. It will be appreciated that the load to be supported by the auxiliary inlet support is only a very small fraction of the load supported by the pivotable support arm, so that this auxiliary inlet support 41, 43 is not very bulky.

The pivotable support arm 32 is pivoted by means of an electric motor (not shown in the drawings), which has to warrant a very precise angular positioning of the heavy beam delivery line 24. The electric motor may drive the support arm 32 e.g. via a chain-drive (not shown in the drawings), wherein geared ring with a large diameter (not shown in the drawings) is fastened to the support arm 32. Other motors, such e.g. hydraulic motors, and/or other drive means, such e.g. a gear wheel drive, are however not excluded. To compensate the substantial weight of this beam delivery line 24, the pivotable support arm 32 forms a support arm extension 40 beyond the axis of rotation 18 to support a counterweight 42 on the other side of the axis of rotation 18. This counterweight 42 is dimensioned to equilibrate the moment about the axis of rotation 18 due to the weight of the beam delivery line 24, so that the pivotable support arm 32 with the heavy beam delivery line 24 can be precisely pivoted about the axis of rotation 18 by a relatively small electric motor. This motor may e.g. drive the support arm 32 by means of a gear-, belt- or chain-drive. One may of course use any another type of drive, suitable for precisely rotating the pivotable support arm 32 by a given angle about the axis of rotation 18.

The support structure 34 of the pivotable support arm 32 comprises two substantially identical supports elements 44, 44'. The pivotable support arm 32 is arranged between these supports elements 44, 44' and comprises two pivot axles 46, 46' arranged symmetrically with regard to the plane of symmetry 36 of the support arm 32. Each of these pivot axles 46, 46' is rotatably supported in a support bearing 48, 48', such as that one shown in FIG. 3. In the support structure 34, both support bearings 48, 48' for the pivot axles 46, 46' of the beam support arm 32 are substantially symmetric with regard to the plane of symmetry 36 containing the center of gravity of the beam delivery line 24. The horizontal distance between the two support elements 44, 44' is less than one third of the distance between the entrance point of the beam 12 into the beam delivery line 24 and the isocenter 22.

Figure 2:
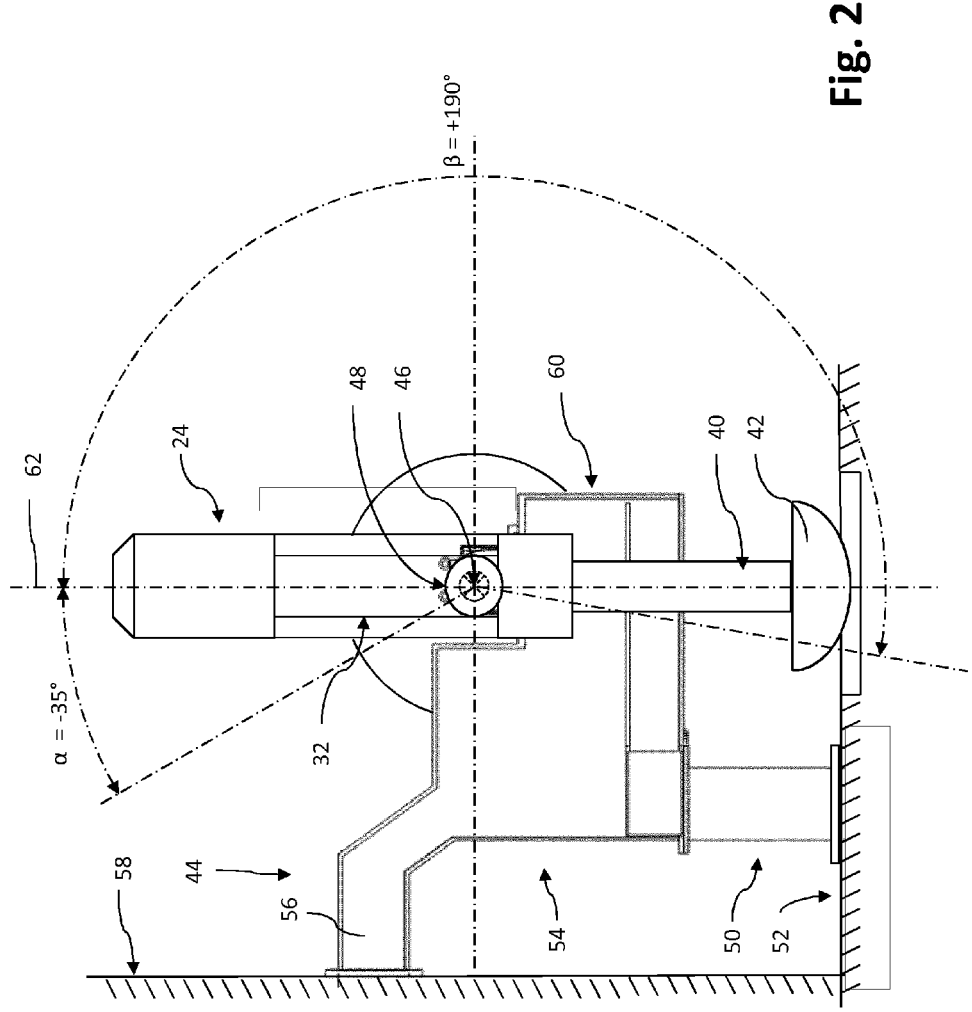
FIG. 2: is a schematic sectional view along line 2-2' of the gantry structure shown in FIG. 1.
Figure 3:
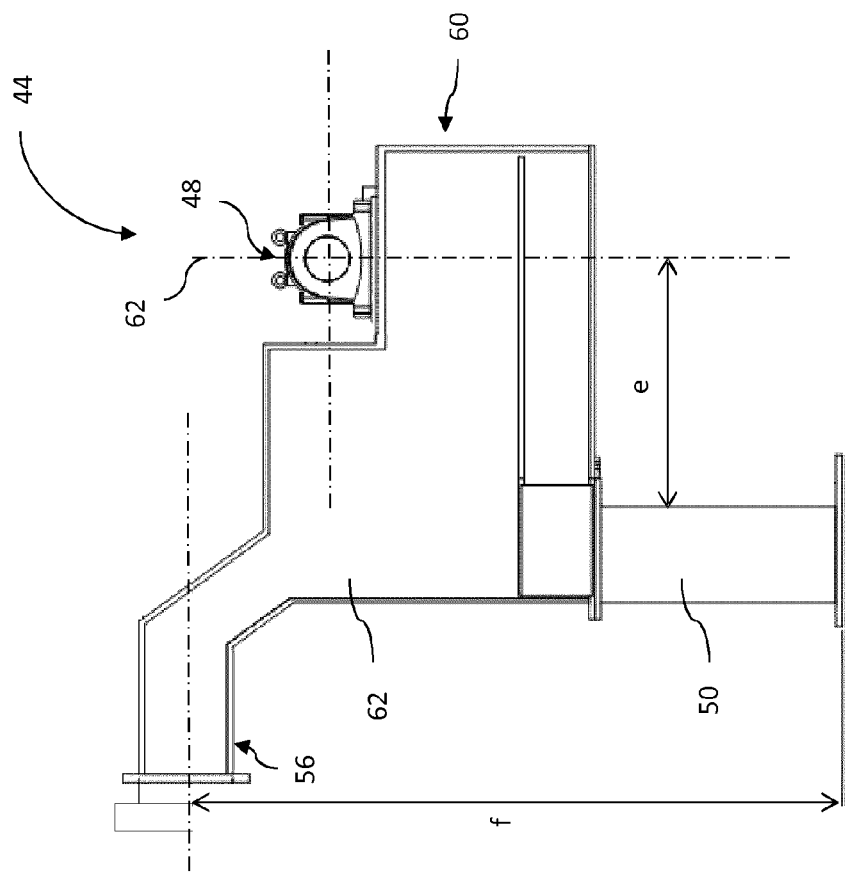
FIG. 3: is schematic elevation view of a support element of the of the gantry structure shown in FIG. 1 and FIG. 2.

Referring now to FIGS. 2 and 3, one of the two substantially identical support element 44, 44' will be described in greater detail. It includes a lower support part 50 for supporting it on a supporting surface 52, typically a horizontal floor, an upper part 54 with a lateral fixing arm 56 for fixing it to a lateral structure 58, such as e.g. a concrete wall, and a cantilever support arm 60. The latter is arranged between the lower part 50 and the upper part 54 for supporting the support bearing 48 at the opposite side of the lateral fixing arm 56 in a cantilevered manner at a certain horizontal distance e from the lower support part 50. This clearance e allows pivoting the beam delivery line 24 by more than 180° as shown in FIG. 2, i.e. allows pivoting it below the axis of rotation 18 across a vertical plane 62 that contains this axis of rotation 18 (in this position the beam is directed upwards). It will also be noted that the lateral fixing arm 56 provides an important lever "f" for compensating the substantial tilting moment exerted onto the support elements 44, 44' by the cantilevered support of the support bearings 48 on theses support elements 44, 44'. Finally, the cantilever support arm 60 is designed so as to have a very high section modulus, i.e. to suffer only very small bending deformations under the considerable weight of the beam delivery line 24. The substantial height of the cantilever support arm 60 allows achieving this high section modulus.

Referring to FIG. 2, it will be noted that cantilever support arm 60 supports the pivotable support arm 32 so as to allow the beam delivery line 24 to rotate about the axis of rotation 18 by an angle greater than 180°. It follows that the beam delivery line 24 is capable of passing in an upper and lower position through the vertical plane 62 containing the axis of rotation 18. In the apparatus shown in FIG. 2, the beam delivery line 24 is e.g. capable of rotating about the axis of rotation 18 between an angular position of about −35° and an angular position of about +190°, wherein theses angles are measured with respect to the vertical plane containing the axis of rotation 18, an angle of 0° corresponding to the position when the beam delivery line 24 is in its upmost position. This design allows amongst others a safe emergency stop of the rotation of the gantry structure 16 in case of any problem.

To achieve a hadron therapy apparatus with a gantry that can be easily transported, easily introduced into the treatment room and easily assembled in situ, the gantry advantageously consists of a few preassembled gantry modules to be assembled in situ. In a preferred gantry structure, a first preassembled gantry module comprises the beam delivery line 24, including advantageously the rotating joint 38, and the pivotable support arm 32, wherein the pivot axles 46, 46' of the beam support arm 32 may already be pre-fitted with the support bearings 48, 48'. A second, complementary gantry module comprises the support arm extension 40 and, optionally, the counterweight 42 (the latter may also form a separate unit, which is fixed to the support arm extension 40 only at the client's premises).

In an alternative embodiment of the gantry, a first preassembled module consists of the beam delivery line 24, including advantageously the rotating joint 38, but excluding the pivotable support arm 32. A first embodiment of a second, complementary gantry module then consists of the pivotable support arm 32, wherein the pivot axles 46, 46' of the beam support arm 32 may advantageously be preassembled with the support bearings 48, 48'. In this case, a third complementary gantry module consists of the support arm extension 40 and, optionally, the counterweight 42 (wherein the latter may also form a separate unit, which is fixed to the support arm extension 40 only at the client's premises). A second, alternative embodiment of the second gantry module, which is complementary to the first preassembled gantry module consisting of the beam delivery line 24, comprises the pivotable support arm 32 and the support arm extension 40, which are both pre-assembled, and optionally, also the counterweight 42 already connected to the support arm extension 40 (wherein the counterweight 42 may also form a separate unit, which is fixed to the support arm extension 40 only at the client's premises).

Figure 4:
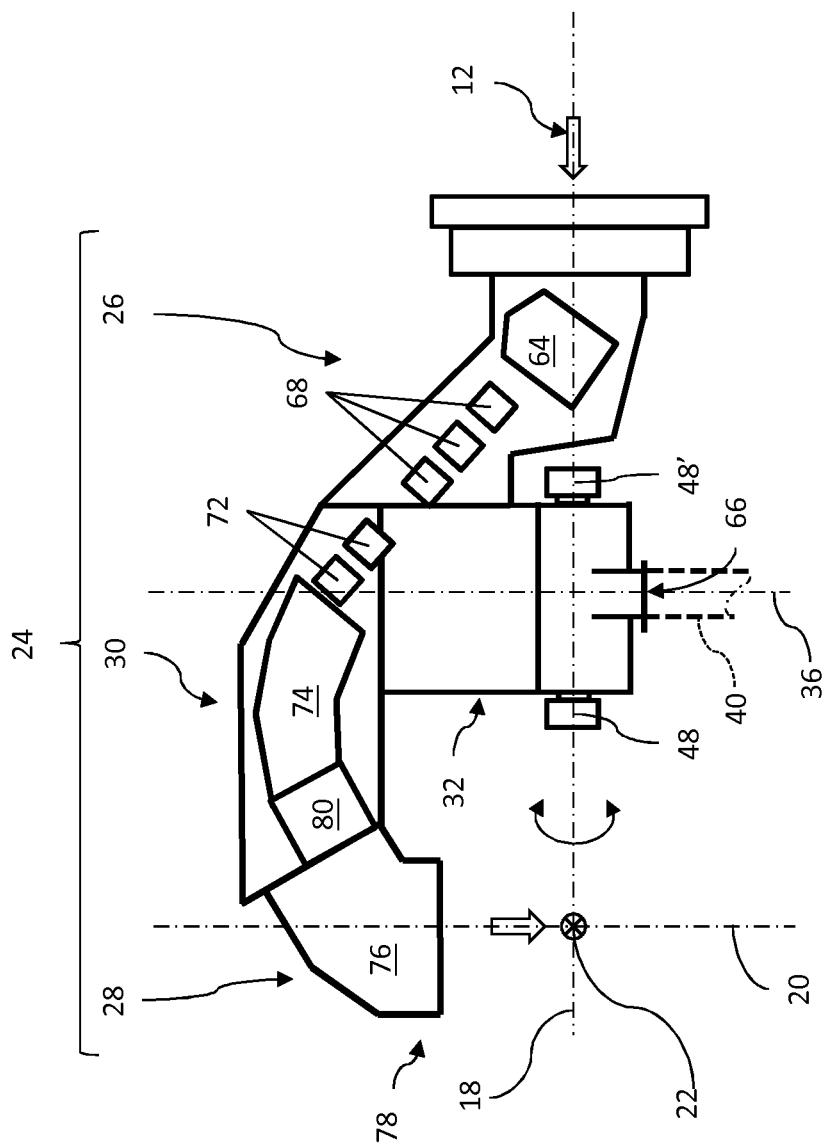
FIG. 4: is schematic partial section of a beam line of the gantry structure shown in FIG. 1.

FIG. 4 shows a schematic representation of a preferred arrangement of the first preassembled gantry module. The latter advantageously comprises the rotating joint 38, three successive beam line units 26, 30 and 28, and the pivotable support arm 32. In this embodiment, the second gantry module, which is formed by the support arm extension 40 with the counterweight 42, is fastened in situ to a flange 66 of the pivotable support arm 32.

The first beam line unit 26, which forms the inlet section 26 of the beam delivery line 24, basically contains a first bending magnet 64 deviating the beam away from the axis of rotation 18, and quadrupole magnets 68. The second beam line unit 30, which forms the middle section of the beam delivery line 24, basically contains further quadrupole magnets 72 and a second bending magnet 74 inflecting the beam, which has been focused and/or defocused in the quadrupole magnets 68 and 72. The third beam line unit 28, which forms the outlet section of the hadron beam, basically contains a third bending magnet 76 and a nozzle 78 for directing the hadron beam at the isocenter 22 in a direction essentially perpendicular to said axis of rotation 18. The second beam line unit 30 may further comprise a scanning magnet 80.

Referring again to FIG. 1, it will be noted that the first beam line unit 26 is supported on a first lateral side of the support arm 32. The second beam line unit 30 is supported on the top side of the pivotable support arm 32, so as to form a cantilever on the second side of the pivotable support arm 32. The third beam line unit 28 is supported in a cantilever manner by the second beam line unit 30.

It will be appreciated that the first gantry module is preferably preassembled at the facility of the manufacturer, i.e. before shipping the different components of the gantry structure 16 to the client's premises. The reduced dimensions and the particular shape of the first gantry module allow to transport it as a unit by truck to the client's premises (typical overall loading dimensions are e.g.: maximum width 3 m; maximum height 4.25 m, maximum length 9 m). The support structure 34, consisting of the two support elements 44, 44', is advantageously delivered as a separate support kit, but it may also be constructed in situ by a local steelwork company. In the client's premises, the first preassembled gantry module is arranged centrally between the two support elements 44, 44' of the support structure 34, with the nozzle 78 and the support arm 32 pointing upwards. It is slightly lifted so that the support bearings 48, 48' can be fixed onto the cantilever support arms 60 of support structure 34 (or so that the pivot axles 46, 46' can be vertically introduced into the open support bearings 48, 48', if the latter are already mounted on the cantilever support arms 60), wherein the pivotable support arm 32 remains hereby in an angular position of 180°, i.e. the beam delivery line 24 is in a rotational equilibrium position about the axis of rotation 18, close to the supporting surface 52. Thereafter, the second gantry module is mounted onto the first gantry module by fixing the support arm extension 40 to the flange 66 of the first gantry module. Thus, the installation time of the gantry structure and the number of assembly operators required at the client's premises are substantially reduced.

The hadron therapy apparatus described hereinbefore has a gantry structure 16 that is less cumbersome and less heavy than any prior art gantry previously used in hadron therapy. The new design of the hadron therapy apparatus can be more compact than with any prior art gantry. It allows moreover an easier integration of the hadron therapy apparatus into the treatment room. For example, in the embodiment shown in FIG. 2, the width c of the pivotable support arm 32 between the beam delivery line 24 and the axis of rotation 18 is about 1.7 m, that is less than 30%, e.g. about 25%, of the distance between the entrance point of the beam 12 into the beam delivery line 24 and the isocenter 22, and the width b of the support arm 32 between the counterweight 42 and the axis of rotation 18 is about 0.45 m. Furthermore, the arrangement of the support structure in the middle of the beam delivery line 24, i.e. close the center of the gantry structure 16, warrants a more equilibrated and simpler load distribution in the support structure, which makes mechanical deflections easier avoidable and residual mechanical deflections more predictable, thereby reducing positioning errors and/or making them at least more predictable. Finally, the gantry structure 16 can be easily designed as a set of preassembled modules that can be easily shipped, easily introduced into the future treatment room and faster assembled therein.

| Reference signs list | |
| --- | --- |
| 10 | hadron accelerator |
| 12 | beam of accelerated hadrons |
| 14 | last section of a beam transport line |
| 16 | gantry structure |
| 18 | axis of rotation |
| 20 | plane perpendicular to the axis of rotation and passing through the isocenter 22 |
| 22 | isocenter |
| 24 | beam delivery line |
| 26 | inlet section of 24 (first beam line unit) |
| 28 | outlet section of 24 (third beam line unit) |
| 30 | middle section of 24 (second beam line unit) |
| 32 | pivotable support arm |
| 34 | support structure (44 + 44') |
| 36 | plane of symmetry of 32 |
| 38 | rotating joint |
| 39 | cylindrical bearing surface on 26 |
| 40 | extension of 32 (support arm extension) |
| 41 | auxiliary inlet support |
| 42 | counter weight |
| 43 | roller support |
| 44, 44' | support elements |
| 46, 46' | pivot axles |
| 48, 48' | support bearings |
| 50 | lower support part of 44 |
| 52 | supporting surface |
| 54 | upper part of 44 |
| 56 | lateral fixing arm of 44 |
| 58 | lateral structure |
| 60 | cantilever support arm on 44, 44' |
| 62 | vertical plane that contains the axis of rotation 18 |
| 64 | first bending magnet |
| 66 | flange on 32 |
| 68 | quadrupole magnets |
| 72 | quadrupole magnets |
| 74 | second bending magnet |
| 76 | third bending magnet |
| 78 | nozzle |
| 80 | scanning magnet |

The invention claimed is:

1. A gantry structure designed for pivoting about an axis of rotation and for delivering a hadron beam on a target, said gantry structure comprising:
    a beam delivery line receiving said hadron beam in a direction essentially parallel to said axis of rotation, deviating it away from said axis of rotation and delivering it so that an axis of the beam intersects said axis of rotation;
    a counterweight supported on the other side of said axis of rotation for compensating a moment of force due to the weight of said beam delivery line; and
    a pivotable support arm supported by a support structure so as to be capable of pivoting about said axis of rotation, wherein said beam delivery line is a self-supporting structure supported by said pivotable support arm in proximity of a center of gravity of the beam delivery line, wherein said counterweight is supported by an extension of said support arm, and wherein said pivotable support arm has a plane of symmetry that is perpendicular to said axis of rotation and contains the center of gravity of said beam delivery line.

2. The gantry structure according to claim 1, wherein said support arm extension is detachably connected to said support arm.

3. The gantry structure according to claim 1, wherein said support structure comprises two support elements, said pivotable support arm being arranged between said two support elements and supported by the latter on two sides.

4. The gantry structure according to claim 3, wherein each of said support elements includes:

a lower part for supporting it on a supporting surface;

an upper part with a lateral fixing arm for fixing it to a lateral structure; and a cantilever support arm arranged between said lower part and said upper part for supporting said pivotable support arm at the opposite side of said lateral fixing arm at a certain horizontal distance (e) from said lower part, so as to allow said beam delivery line to rotate about said axis of rotation by an angle greater than 180°, wherein said beam delivery line is capable of passing from an upper to a lower position and vice versa through a vertical plane containing said axis of rotation.

5. The gantry structure according to claim 1, wherein said beam delivery line is capable of rotating about said axis of rotation between an angular position of about $-\alpha°$ and an angular position of about $+\beta°$, wherein theses angles are measured with respect to a vertical plane containing said axis of rotation, an angle of 0° corresponding to the position when said beam delivery line is in its upmost position.

6. The gantry structure according to claim 1, wherein said beam delivery line comprises:

a first beam line unit;
a second beam line unit; and
a third beam line unit;
wherein:
said support arm has a first side facing an inlet of the hadron beam into said beam delivery line and a second side facing an outlet of the hadron beam of said beam delivery line and a top side;

said first beam line unit is supported on said first side of said support arm;

said second beam line unit is supported on the top side of said pivotable support arm, so as to form a cantilever on said second side of said pivotable support arm; and said third beam line unit is supported in a cantilever manner by said second beam line unit.

7. The gantry structure according to claim 6, wherein:

said third beam line unit further includes a nozzle for delivering said hadron beam at an isocenter; and/or said second beam line unit further includes a scanning magnet.

8. The gantry structure according to claim 1, further comprising an auxiliary inlet support arranged near a beam inlet end of said beam delivery line and configured for centering said beam delivery line with regard to a fixed beam transport line to which said beam delivery line is connected.

9. The gantry structure according to claim 8, wherein said auxiliary inlet support includes a roller support located beneath said beam inlet end of said beam delivery line, where it cooperates with a cylindrical bearing surface arranged on said beam inlet end for centering the latter on the axis of rotation.

10. The gantry structure according to claim 1, wherein the target to be irradiated is located at an isocenter located at the axis of rotation, and wherein the hadron beam is delivered so that the axis of the beam intersects said axis of rotation at said isocenter.

11. The gantry structure according to claim 1, wherein a width (c) of the pivotable support arm is less than 30% of a distance between an entrance point of the hadron beam into the beam delivery line and a point where the axis of the beam intersects said axis of rotation.

12. A hadron therapy apparatus comprising the gantry structure according to claim 1.

13. A method for constructing a gantry structure as claimed in claim 1, the method comprising assembling said gantry structure in situ from a few pre-assembled gantry modules, one of said pre-assembled gantry modules comprising said beam delivery line and said pivotable support arm, said pivotable support arm having a plane of symmetry that is perpendicular to said axis of rotation and contains the center of gravity of said beam delivery line.

14. The method as claimed in claim 13, wherein:

said preassembled gantry module comprising said beam delivery line and said pivotable support arm is arranged on a supporting surface centrally between two support elements of the support structure, with the support arm pointing upwards; and said preassembled gantry module is then slightly lifted so that either support bearings mounted on pivot axles of the support arm can be fixed onto the support structure, or so that pivot axles of the support arm can be vertically introduced into open support bearings mounted on the support structure;

wherein the pivotable support arm remains in a position in which the beam delivery line is in a rotational equilibrium position about the axis of rotation, close to the supporting surface.

15. The gantry structure according to claim 3, wherein each of said support elements comprises a support bearing in which a bearing pivot of said pivotable support arm is received.

16. The gantry structure according to claim 5, wherein said beam delivery line is capable of rotating about said axis of rotation between an angular position of about $-\alpha°$ and an angular position of about $+\beta°$, wherein ranges for $\alpha°$ and $\beta°$ are: $15°<\alpha<45°$ and $180°<\beta<200°$.

17. The gantry structure according to claim 6, wherein said first beam line unit contains a first bending magnet and at least two quadrupole magnets.

18. The gantry structure according to claim 6, wherein said second beam line unit contains at least two quadrupole magnets and a second bending magnet.

19. The gantry structure according to claim 6, wherein said third beam line unit contains a third bending magnet.

* * * * *